(12) United States Patent
Kouka et al.

(10) Patent No.: US 7,728,181 B2
(45) Date of Patent: Jun. 1, 2010

(54) METHOD FOR PRODUCING α, β-UNSATURATED ETHER

(75) Inventors: Hiroto Kouka, Kawasaki (JP); Yoshikuni Okumura, Kawasaki (JP)

(73) Assignee: Showa Denko K.K., Tokyo (JP)

( * ) Notice: Subject to any disclaimer, the term of this patent is extended or adjusted under 35 U.S.C. 154(b) by 0 days.

(21) Appl. No.: 12/162,531

(22) PCT Filed: Jan. 26, 2007

(86) PCT No.: PCT/JP2007/051245

§ 371 (c)(1), (2), (4) Date: Dec. 17, 2008

(87) PCT Pub. No.: WO2007/086496

PCT Pub. Date: Aug. 2, 2007

(65) Prior Publication Data

US 2009/0227818 A1    Sep. 10, 2009

(30) Foreign Application Priority Data

Jan. 30, 2006  (JP) .............................. 2006-021344
Aug. 31, 2006  (JP) .............................. 2006-236787

(51) Int. Cl.
*C07C 41/28*   (2006.01)

(52) U.S. Cl. .................................................... 568/691

(58) Field of Classification Search .................. 568/691
See application file for complete search history.

(56) References Cited

U.S. PATENT DOCUMENTS 4,014,941 A    3/1977   Tanaka et al.

FOREIGN PATENT DOCUMENTS

| | | |
|---|---|---|
| JP | 49-045382 B1 | 12/1974 |
| JP | 54-001683 B1 | 1/1979 |
| JP | 57-185232 A | 11/1982 |
| JP | 58-032838 A | 2/1983 |
| JP | 05-229977 A | 9/1993 |

*Primary Examiner*—Sikarl A Witherspoon
(74) *Attorney, Agent, or Firm*—Sughrue Mion, PLLC

(57) ABSTRACT

Disclosed is a method for producing an α,β-unsaturated ether efficiently and stably for a long time. In the method for producing an α,β-unsaturated ether, an acetal is thermally decomposed in the presence of a catalyst containing an apatite represented by any of the following formula (1)-(4)

$$(M)_{5-y}(HZO_4)_y(ZO_4)_{3-y}(X)_{1-y} \quad (1)$$

$$(M)_{5-y}(HPO_4)_y(PO_4)_{3-y}(X)_{1-y} \quad (2)$$

$$(M)_{5-y+2n}(HZO_4)_y(ZO_4)_{3-y}(X)_{1-y}(SiO_4)_n \quad (3)$$

$$(M)_{5-y+m}(HZO_4)_y(ZO_4)_{3-y}(X)_{1-y}(CO_3)_m \quad (4).$$

3 Claims, 4 Drawing Sheets

[FIG. 1]
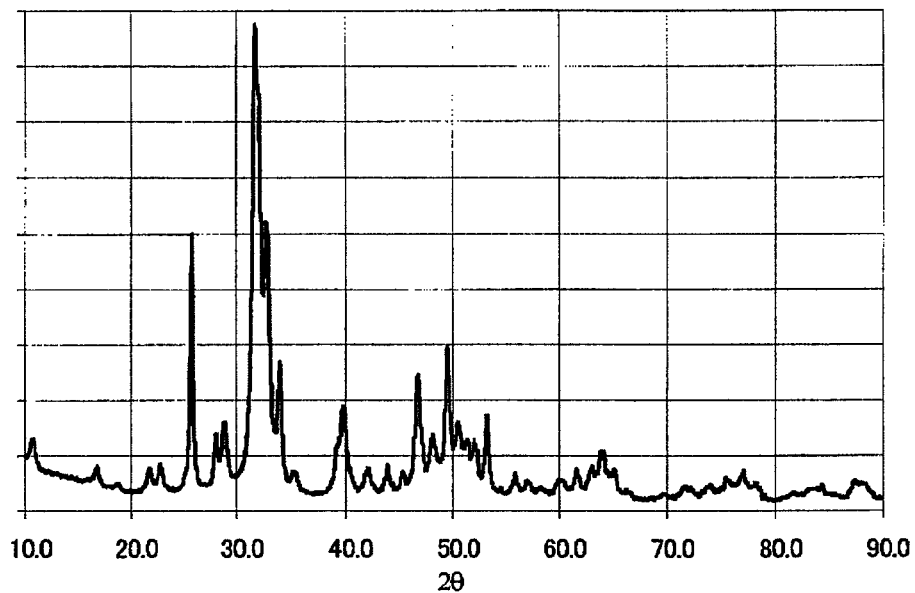
[FIG. 2]
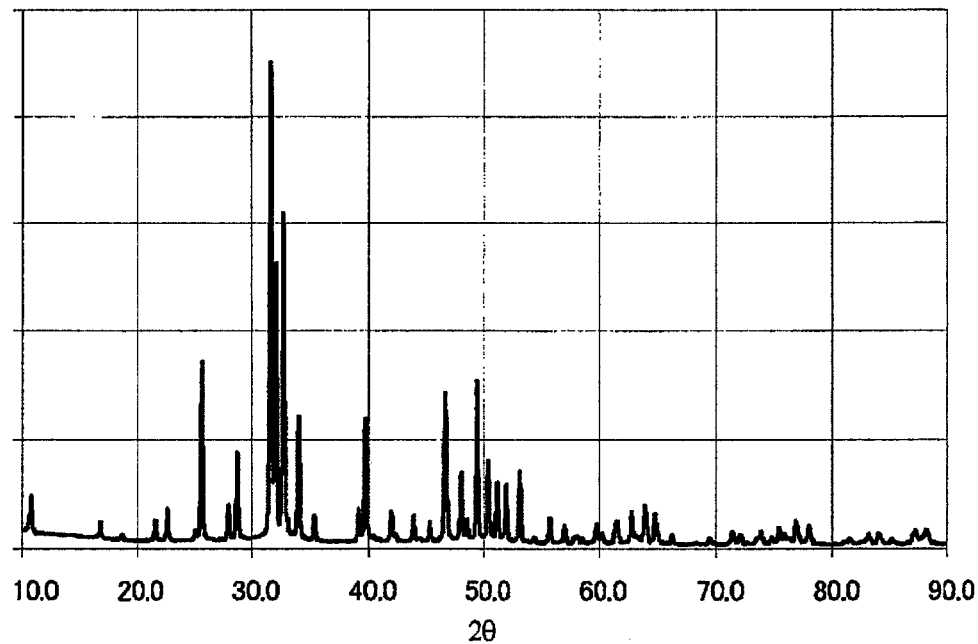

[FIG. 3]
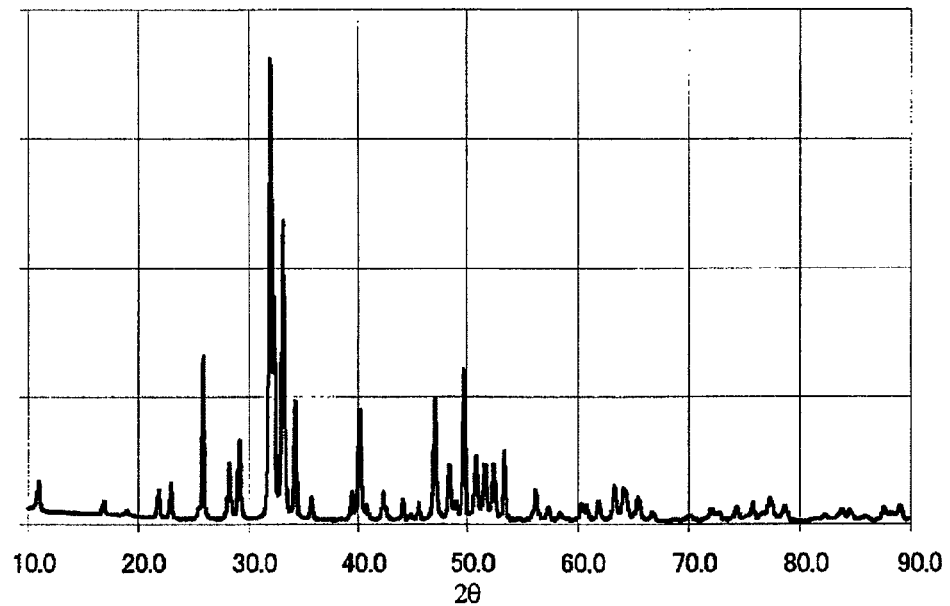
[FIG. 4]
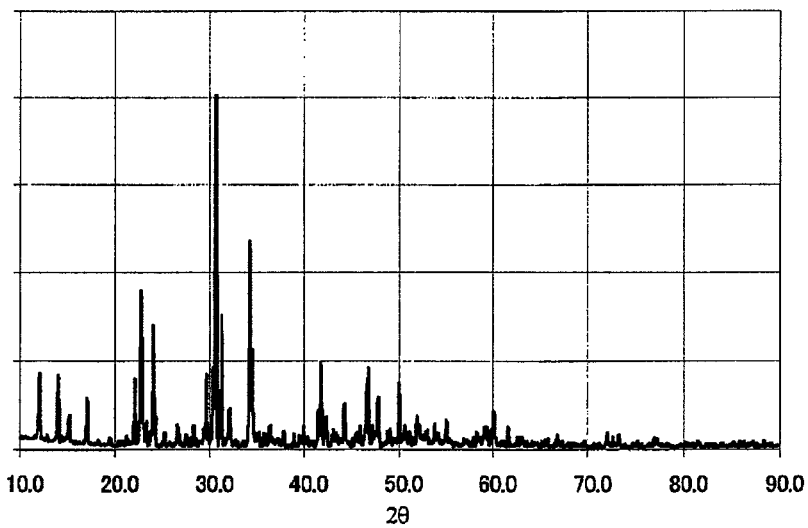

[FIG. 5]
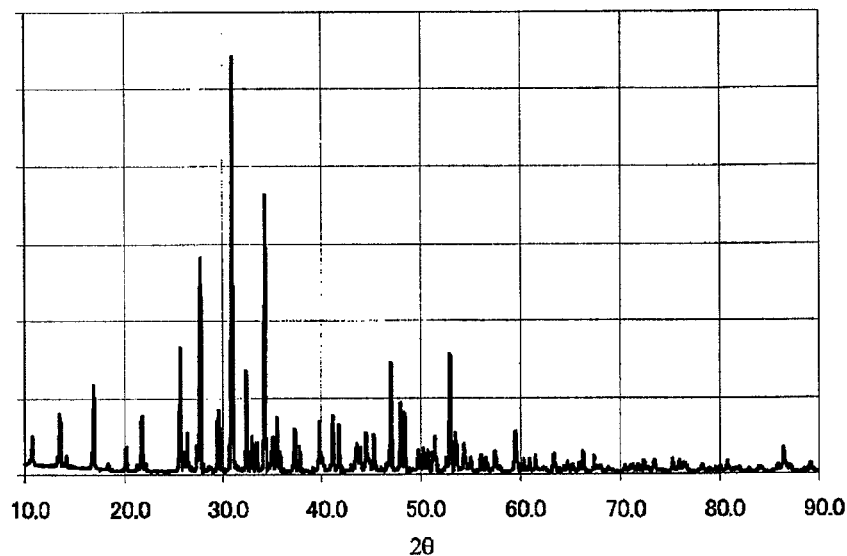
[FIG. 6]
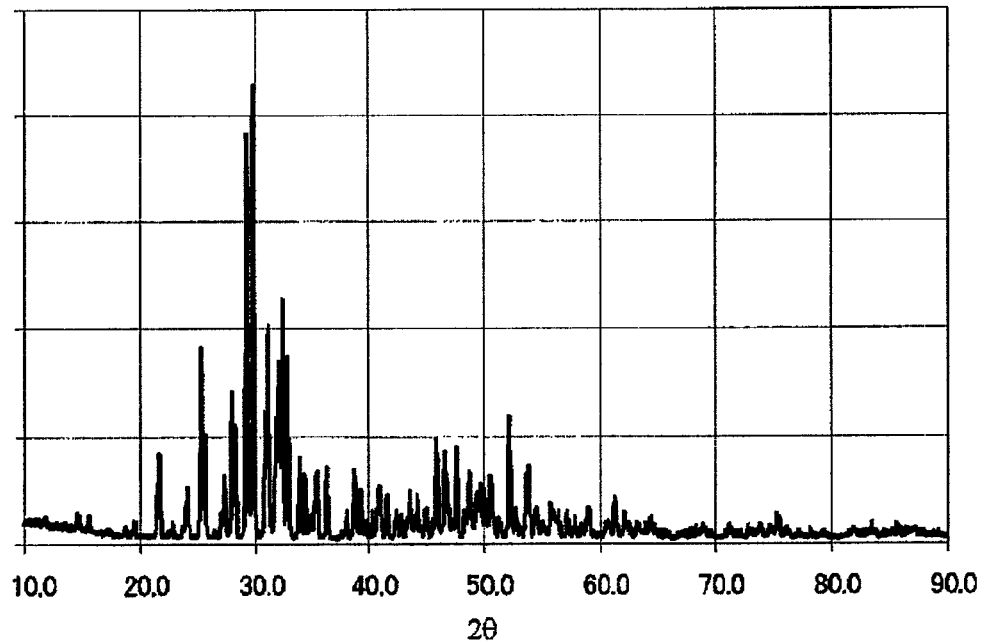

[FIG. 7]
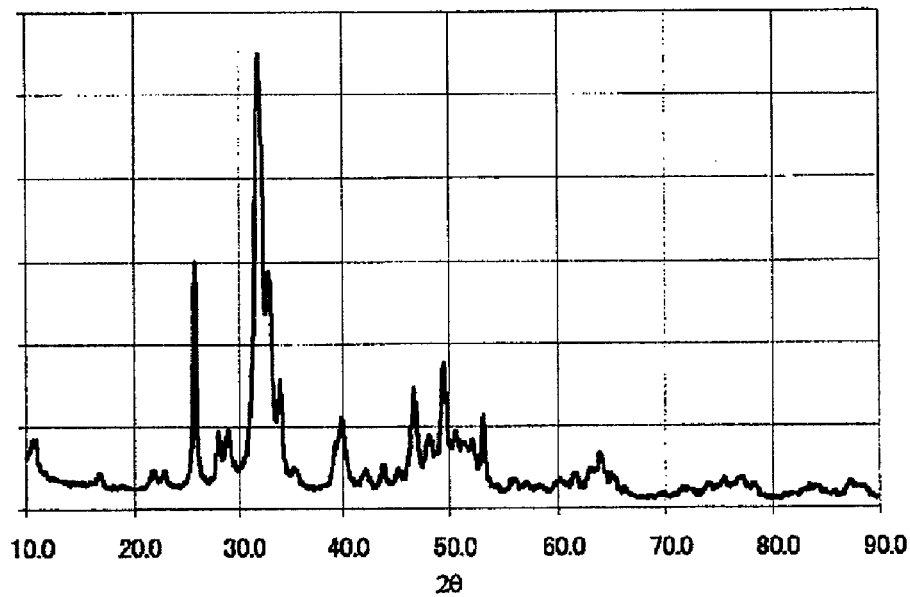
[FIG. 8]
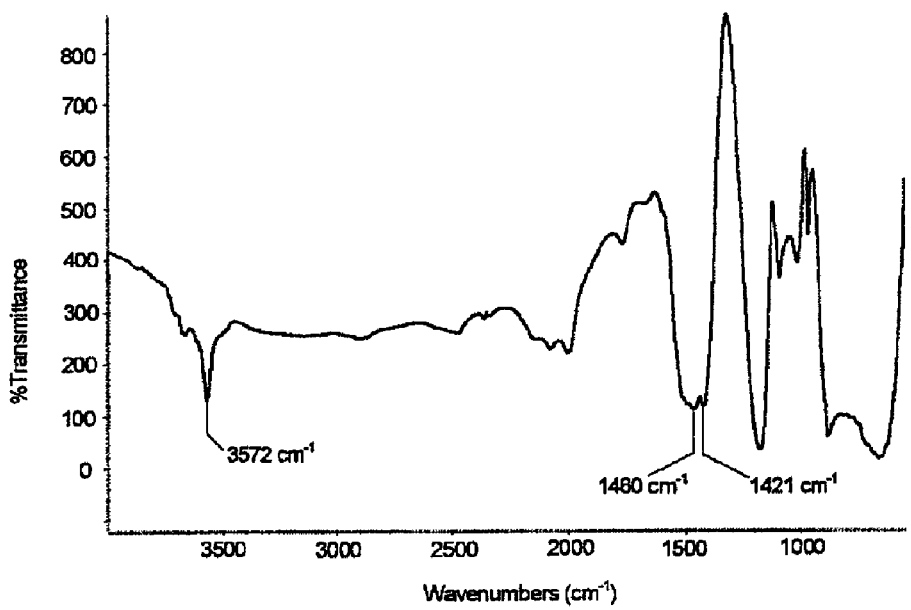

METHOD FOR PRODUCING α,β-UNSATURATED ETHER

TECHNICAL FIELD

The present invention relates to a method for producing an α,β-unsaturated ether.

BACKGROUND ART

Either by homopolymerization or by copolymerization with other substances, α,β-unsaturated ethers are industrially important substances for many types of synthetic resins, adhesives, lubricating oils and as intermediates for drugs, agricultural chemicals, perfumes, etc. Thermolysis of acetals is commonly known as a method for producing α,β-unsaturated ethers. In general, a catalyst is used in the thermolysis reaction.

With respect to such catalysts, patent document 1 discloses sulfates of metals having a higher ionization tendency than hydrogen, and catalysts wherein these metal sulfates are supported on a solid carrier such as alumina or silica gel. The patent document illustrates the supported catalysts by describing catalysts wherein calcium sulfate, manganese sulfate, etc. are supported on alumina, magnesium silicate, etc. Although these catalysts show relatively high catalytic performance in terms of conversion of raw materials, there are cases where the selectivity is inadequate. The document does not consider the life of the catalysts.

There are also disclosed carbonates and molybdates (for example, refer to patent document 2), and oxides or carbonates of alkali metals or alkaline earth metals (for example, refer to patent document 3). These are inadequate in terms of catalytic performances such as degree of conversion and selectivity, and are severely degraded due to coking. Furthermore, the mechanical strength of the catalysts is poor, and there are concerns over problems such as catalyst fragmentation when the catalysts are used in actual plants.

Furthermore, silica/magnesia (for example, refer to patent document 4), niobic acids (for example, refer to patent document 5), magnesium oxide (for example, refer to patent document 6), and base-treated zeolites (for example, refer to patent document 7) are also cited as examples of the reaction catalysts. However, these catalysts too have poor catalytic performances such as conversion and selectivity, and large amounts of coke are deposited to shorten the catalyst life.

A patent wherein a calcium salt of phosphoric acid is used as a catalyst to effect thermolysis of an acetal is also disclosed (for example, refer to patent document 8) In detail, calcium phosphate $Ca_3(PO_4)_2$, calcium hydrogen phosphate $CaH(PO_4)$, etc. are used to catalyze thermolysis reaction of acetaldehyde diisobutyl acetal. However, these catalysts too have inadequate catalytic performances such as conversion and catalyst life.

On the other hand, a method which uses lithium phosphate (for example, refer to patent document 9) as a catalyst is disclosed. Although this catalyst shows relatively high catalytic performance in terms of selectivity and suppresses coke deposition, the degree of conversion is inadequate.

There are also disclosed a catalyst system wherein lithium phosphate is supported on silica (for example, refer to patent document 10) and a catalyst system wherein a salt of an alkali metal or alkaline earth metal is added to a mixture of lithium phosphate and silica sol (for example, refer to patent document 11). However, these catalyst systems have insufficient conversion.

Therefore, there has been a demand for reaction catalysts which simultaneously satisfy both high catalytic performance and long catalyst life, and which can efficiently and stably produce an α,β-unsaturated ether for a long time.

[Patent Document 1] Japanese Examined Patent Application Publication No. S41-5376
[Patent Document 2] Japanese Examined Patent Application Publication No. S49-45382
[Patent Document 3] Japanese Unexamined Patent Application Publication No. S57-139030
[Patent Document 4] Japanese Unexamined Patent Application Publication No. H10-175904
[Patent Document 5] Japanese Unexamined Patent Application Publication No. H09-143117
[Patent Document 6] Japanese Unexamined Patent Application Publication No. H08-277237
[Patent Document 7] Japanese Unexamined Patent Application Publication No. S62-87247
[Patent Document 8] Japanese Examined Patent Application Publication No. S54-1683
[Patent Document 9] Japanese Unexamined Patent Application Publication No. H05-229977
[Patent Document 10] Japanese Unexamined Patent Application Publication No. S58-32838
[Patent Document 11] Japanese Unexamined Patent Application Publication No. S57-185232

DISCLOSURE OF THE INVENTION

Problems to be Solved by the Invention

The present invention has an object of providing a method for efficiently and stably producing an α,β-unsaturated ether for a long time.

Means for Solving the Problems

The inventors of the present invention diligently studied to solve the above-mentioned problems. They have then found that catalyst systems having specific apatites as catalytic components possess high catalytic activity, high selectivity and long catalyst life, and the catalyst systems solve the above-described problems. The present invention has been completed based on the findings.

The present invention relates to the following:

[1]

A method for producing an α,β-unsaturated ether comprising thermally decomposing an acetal in the presence of a catalyst containing an apatite, the apatite being represented by general formula (1):

$$(M)_{5-y}(HZO_4)_y(ZO_4)_{3-y}(X)_{1-y} \quad (1)$$

wherein M is at least one selected from the group consisting of Mg, Ca, Sr, Ba, Pb, Mn and Cd, Z is at least one selected from the group consisting of P, As and Sb, X is at least one selected from the group consisting of OH, F, Cl, Br, I and At, and $0 \leq y < 1$.

[2]

A method for producing an α,β-unsaturated ether comprising thermally decomposing an acetal in the presence of a catalyst containing a phosphate apatite, the apatite being represented by general formula (2):

$$(M)_{5-y}(HPO_4)_y(PO_4)_{3-y}(X)_{1-y} \quad (2)$$

wherein M is at least one selected from the group consisting of Mg, Ca, Sr, Ba, Pb, Mn and Cd, X is at least one selected from the group consisting of OH, F, Cl, Br, I and At, and $0 \leq y < 1$.

[3]

A method for producing an α,β-unsaturated ether comprising thermally decomposing an acetal in the presence of a catalyst containing an apatite, the apatite being represented by general formula (3) or (4):

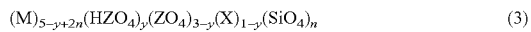
(3)

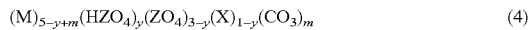
(4)

wherein M is at least one selected from the group consisting of Mg, Ca, Sr, Ba, Pb, Mn and Cd, Z is at least one selected from the group consisting of P, As and Sb, X is at least one selected from the group consisting of OH, F, Cl, Br, I and At, $0 \leq y < 1$, $0 < n < 3$, and $0 < m < 3$.

EFFECTS OF THE INVENTION

The production method of the present invention uses a catalyst which has a long catalyst life and which maintains high catalytic activity and selectivity for a long time, and an α,β-unsaturated ether may be produced efficiently and stably. According to the production method of the present invention, the catalyst maintains high catalytic activity and selectivity for a long time regardless of the type of acetal used as the reaction raw material, and the above benefits are reliably obtained.

BRIEF DESCRIPTION OF THE DRAWINGS

FIG. 1 shows the results of X-ray powder diffraction measurement of the catalyst used in Example 4.

FIG. 2 shows the results of X-ray powder diffraction measurement of the catalyst used in Example 5.

FIG. 3 shows the results of X-ray powder diffraction measurement of the catalyst used in Example 6.

FIG. 4 shows the results of X-ray powder diffraction measurement of the catalyst used in Comparative Example 6.

FIG. 5 shows the results of X-ray powder diffraction measurement of the catalyst used in Comparative Example 7.

FIG. 6 shows the results of X-ray powder diffraction measurement of the catalyst used in Comparative Example 8.

FIG. 7 shows the results of X-ray powder diffraction measurement of the catalyst used in Example 12.

FIG. 8 shows the results of FT-IR analysis measurement of the catalyst used in Example 12.

BEST MODE FOR CARRYING OUT THE INVENTION

A detailed description of the present invention will now be given.

A production method for α,β-unsaturated ethers of the present invention comprises thermally decomposing an acetal in the presence of a catalyst containing a specific apatite. Here, the term acetal has a broad meaning, including acetals derived from aldehydes and acetals derived from ketones, namely, ketals.

More specifically, in the α,β-unsaturated ether production method of the present invention, an acetal represented by general formula (5) below is thermally decomposed in the gas phase to produce an α,β-unsaturated ether represented by general formula (6) below.

(5)

(6)

In formulae (5) and (6), $R^1$, $R^2$ and $R^3$ each independently represent a hydrogen atom, an alkyl group, an alkenyl group or an aryl group; $R^4$ represents an alkyl group, an alkenyl group or an aryl group; and a plurality of $R^4$ in formula (5) may represent the same or different groups.

In the α,β-unsaturated ether production method of the present invention, examples of the raw material acetals represented by general formula (5) include acetaldehyde dimethyl acetal, acetaldehyde diethyl acetal, acetaldehyde di-n-propyl acetal, acetaldehyde di-n-butyl acetal, acetaldehyde di-iso-butyl acetal, acetaldehyde di-benzyl acetal, propionaldehyde diethyl acetal, butylaldehyde diethyl acetal, 2,2-dimethoxypropane, 2,2-diethoxypropane, and 2,2-dibenzylpropane.

Examples of the α,β-unsaturated ethers of formula (6) produced in the present invention include methyl vinyl ethers, ethyl vinyl ethers, n-propyl vinyl ethers, n-butyl vinyl ethers, isobutyl vinyl ethers, benzyl vinyl ethers, 2-methoxy-1-propene, 2-ethoxy-1-propene, 2-propoxy-1-propene, and 2-butoxy-1-propene.

The apatite used in the α,β-unsaturated ether production method of the present invention is represented by any of general formulae (1)-(4) below, and is preferably represented by general formula (2).

(1)

In formula (1), M is at least one selected from the group consisting of Mg, Ca, Sr, Ba, Pb, Mn and Cd, Z is at least one selected from the group consisting of P, As and Sb, X is at least one selected from the group consisting of OH, F, Cl, Br, I and At, and $0 \leq y < 1$.

(2)

In formula (2), M is at least one selected from the group consisting of Mg, Ca, Sr, Ba, Pb, Mn and Cd, X is at least one selected from the group consisting of OH, F, Cl, Br, I and At, and $0 \leq y < 1$.

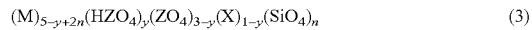
(3)

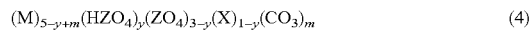
(4)

In formulae (3) and (4), M is at least one selected from the group consisting of Mg, Ca, Sr, Ba, Pb, Mn and Cd, Z is at least one selected from the group consisting of P, As and Sb, X is at least one selected from the group consisting of OH, F, Cl, Br, I and At, $0 \leq y < 1$, $0 < n < 3$, and $0 < m < 3$.

In general, apatite is a collective term for phosphate minerals that have a basic compositional formula represented by formula (1) above and belong to the hexagonal system $P6_{3/m}$ or monoclinic system $P2_{1/b}$. When y=0, the basic compositional formula is $M_5(ZO_4)_3X$, which is called stoichiometric apatite. On the other hand, it is called non-stoichiometric apatite when $0 < y < 1$. In the present invention, both stoichiometric apatites and non-stoichiometric apatites can achieve the advantages of the invention. Of these, the stoichiometric apatites are preferable in terms of activity, selectivity, catalyst life, etc.

The crystalline structure of apatites is extremely stable. This crystalline structure can be easily differentiated from substances having other crystalline structures by publicly known methods such as X-ray diffraction. X-ray diffraction data for hydroxyapatite and fluoroapatite, which are typical apatites, are shown below (Table 1).

In the table, d represents the lattice spacing, and $I/I_1$ represents the diffraction line intensity. The diffraction angle θ is given according to the Bragg conditional expression ($n\lambda=2d\sin\theta$) where n is an integer and λ is the wavelength of the X-rays.

TABLE 1

| Ca5(PO4)3(OH) | | Ca5(PO4)3(F) | |
|---|---|---|---|
| d (Å) | $I/I_1$ | d (Å) | $I/I_1$ |
| 8.17 | 12 | 8.12 | 8 |
| 5.26 | 6 | 5.25 | 4 |
| 4.72 | 4 | 4.68 | <1 |
| 4.07 | 10 | 4.06 | 8 |
| 3.88 | 10 | 3.87 | 8 |
| 3.51 | 2 | 3.49 | <1 |
| 3.44 | 40 | 3.44 | 40 |
| 3.17 | 12 | 3.17 | 14 |
| 3.08 | 18 | 3.07 | 18 |
| 2.81 | 100 | 2.80 | 100 |
| 2.78 | 60 | 2.72 | 55 |
| 2.72 | 60 | 2.70 | 60 |
| 2.63 | 25 | 2.62 | 30 |
| 2.53 | 6 | 2.52 | 6 |
| 2.30 | 8 | 2.29 | 8 |
| 2.26 | 20 | 2.25 | 20 |
| 2.23 | 2 | 2.22 | 4 |
| 2.15 | 10 | 2.14 | 6 |
| 2.13 | 4 | 2.13 | 4 |
| 2.07 | 8 | 2.06 | 6 |
| 2.04 | 2 | 2.03 | 2 |
| 2.00 | 6 | 2.00 | 4 |
| 1.94 | 30 | 1.94 | 25 |
| 1.89 | 16 | 1.88 | 14 |
| 1.87 | 6 | 1.86 | 4 |
| 1.84 | 40 | 1.84 | 30 |
| 1.81 | 20 | 1.80 | 16 |
| 1.78 | 12 | 1.77 | 14 |
| 1.75 | 16 | 1.75 | 14 |
| 1.72 | 20 | 1.72 | 16 |
| 1.68 | 4 | 1.68 | <1 |
| 1.64 | 10 | 1.64 | 6 |
| 1.61 | 8 | 1.61 | 4 |
| $CuK_{\alpha1}$, 1.5405 Å | | 1.58 | 2 |
| | | 1.56 | <1 |
| | | 1.53 | 6 |
| | | 1.52 | 4 |
| | | 1.50 | 4 |
| | | 1.50 | 4 |
| | | $CuK_{\alpha1}$, 1.5405 Å | |

(Source) "Semento-Sekkou-Sekkai Handbook (Handbook of Cement, Gypsum and Lime)", The Society of Inorganic Materials, Japan (Gihodo Shuppan Co., Ltd.)

The apatites used in the present invention may be phosphates (Z=P), arsenates (Z=As) or antimonates (Z=Sb), but are particularly preferably phosphates.

In a stoichiometric phosphate apatite $M_5(PO_4)_3(X)$, X is preferably OH, F or Cl, namely, hydroxyapatite $M_5(PO_4)_3$ (OH), fluoroapatite $M_5(PO_4)_3$ (F), or chloroapatite $M_5(PO_4)_3$ (Cl). These phosphate apatites which contain OH, F or Cl may be pure materials containing no other components, or may be materials containing OH, F and Cl in arbitrary blending ratios.

The hydroxyapatite may be magnesium salt $Mg_5(PO_4)_3$ (OH), calcium salt $Ca_5(PO_4)_3$ (OH), strontium salt $Sr_5(PO_4)_3$ (OH), barium salt $Ba_5(PO_4)_3$(OH), manganese salt $Mn_5(PO_4)_3$ (OH), lead salt $Pb_5(PO_4)_3$(OH), or composite salt of these salts.

Similarly, the fluoroapatite may be magnesium salt $Mg_5(PO_4)_3$(F), calcium salt $Ca_5(PO_4)_3$(F), strontium salt $Sr_5$ $(PO_4)_3$(F), manganese salt $Mn_5(PO_4)_3$(F), barium salt $Ba_5$ $(PO_4)_3$(F), lead salt $Pb_5(PO_4)_3$(F), or composite salt of these salts.

Similarly, the chloroapatite may be magnesium salt $Mg_5$ $(PO_4)_3$(Cl), calcium salt $Ca_5(PO_4)_3$(Cl), strontium salt $Sr_5$ $(PO_4)_3$(Cl), barium salt $Ba_5(PO_4)_3$(Cl), manganese salt $Mn_5$ $(PO_4)_3$ (Cl), lead salt $Pb_5$ $(PO_4)_3$(Cl), or composite salt of these salts.

In particular, the catalyst preferably contains magnesium, calcium, strontium or barium phosphate apatite as a principal component. More particularly, using calcium phosphate apatites is preferable in the α,β-unsaturated ether production method of the present invention.

In addition to apatites (hydroxyapatites, fluoroapatites, chloroapatites), many types of calcium phosphates are known, such as $Ca_3(PO_4)_2$(α-, β-), $CaHPO_4$, $Ca_2P_2O_7$, $Ca_4$ $(PO_4)_2O$, etc. It is known from research carried out in the past that the catalytic performance of calcium phosphates in various reactions differs depending on the type of calcium phosphate. For example, in ethanol decomposition reactions using calcium phosphates as catalysts, it was reported that a dehydration reaction occurred with $Ca_3(PO_4)_2$ (α-, β-), and that a dehydrogenation reaction occurred with apatites. (Reference document) H. Monma, J. Catalysis 75, 200-203 (1982)

In the α,β-unsaturated ether production method of the present invention, the present inventors have found that, of the calcium phosphates, those having an apatite structure possess specifically excellent catalytic activity, selectivity and life.

The non-stoichiometric apatites are represented by general formulae (1) and (2) wherein 0<y<1, and occur as a result of substitution of part of the $ZO_4$ or $PO_4$ in the stoichiometric apatites with $HZO_4$ or $HPO_4$. The crystalline structures thereof are the same as those of the stoichiometric apatites.

It is known that the phosphate apatites maintain the apatite structure over a wide range of substitution with elements based on the basic compositional formula $(M)_{5-y}(HZO_4)_y$ $(ZO_4)_{3-y}(X)_{1-y}$, which is used in the present invention.

For example, the cations may be substituted by hydrogen atoms, alkalimetal ions, alkaline earth metal ions or transition metal ions. The anions may be substituted by other oxoacid groups or other anions. For example, silicate apatites wherein part of the phosphate ions are substituted by silicate groups and carbonate apatites wherein part of the phosphate ions are substituted by carbonate groups are known. The silicate apatites are represented by formula (3) above, and the structure of carbonate apatites is represented by formula (4) above. The apatites may contain water of hydration.

When the apatite is substituted with these other ions, the M/P ratio changes depending on the degree of substitution. The advantages of the present invention are achieved even if the apatite is substituted by these other ions as long as the apatite structure is maintained.

The reasons why the apatite structure is specifically advantageous to the reaction in the invention are probably as follows. First, it is thought that the acetal decomposition reaction is promoted by the simultaneous actions of the Lewis acidity of the metal cation and the basicity of the X anion in the apatite structure (refer to (A) below). In addition, the apatite crystalline structure is extremely stable even at high temperatures; for example, it is known that the crystalline structure of hydroxyapatite is maintained even when heated to 1000° C. or more. There are very few other examples of hydroxyl groups being held in crystalline structures at such high temperatures. That is, the apatite structure acts beneficially in the reaction probably because the crystalline structure which promotes the acetal decomposition reaction exists stably even at relatively high temperatures within the reaction temperature range. These will be the reasons why the apatite structure imparts the catalyst used in the α,β-unsaturated ether production with the useful properties, i.e., high activity and selectivity and long life.

[Formula 1]

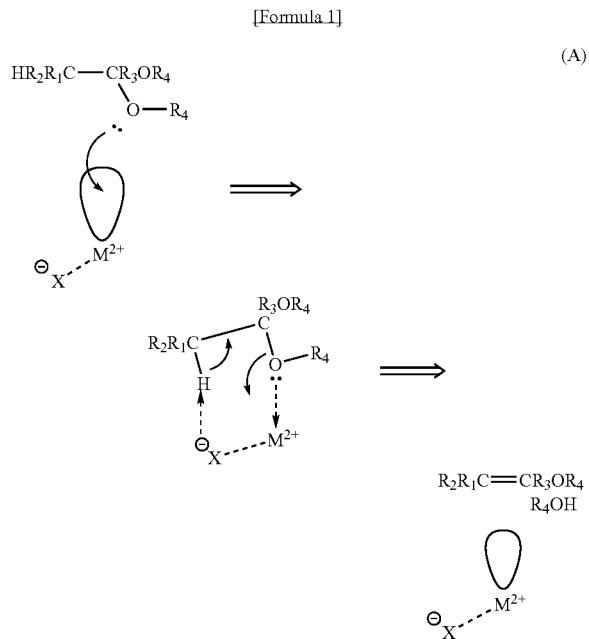

Strength of the acid center, which is the active site in the reaction, in other words, the Hammett acidity $H_0$ of the solid catalyst, may be measured according to, for example, the document (Shokubai Kouza (Catalysis lectures) (Supplement) "Shokubai Jikken Handbook (Handbook of Catalytic Experiments)", Catalysis Society of Japan, Kodansha Scientific, page 170). Indicators used for Hammett acidity are shown below.

TABLE 2

| | Color | | |
|---|---|---|---|
| Indicators | Base-form | Aci-form | pKa |
| Methyl red | yellow | red | +4.8 |
| Phenylazonaphthylamine | yellow | red | +4.0 |
| p-Dimethylaminoazobenzene | yellow | red | +3.3 |
| 2-Amino-5-azotoluene | yellow | red | +2.0 |
| Benzeneazodiphenylamine | yellow | purple | +1.5 |

The maximum Hammett acidity of the surface of the apatite used in the present invention is not particularly restricted, but it is preferable that $+2.0<H_0\leq+4.8$, more preferable that $3.3<H_0\leq+4.8$, and further preferable that $+4.0<H_0\leq+4.8$.

With solid catalysts, the surface area of the solid greatly affects the catalytic activity. In general, if the surface area is small, the number of active sites per unit area is small, leading to a reduction in catalytic activity. With regard to the surface area of the apatite used in the present invention, it is publicly known that materials may be synthesized which have a BET specific surface area as small as 10 m²/g or which have a relatively large BET specific surface area of 50 m²/g or more according to gas adsorption method. The advantages of the invention may be achieved even with catalysts having a small specific surface area.

Apatites are produced naturally as a variety of minerals. The most common form of natural phosphate apatites is fluoroapatite. It is possible to synthesize apatites. Because high-purity materials are suitable for use as the catalyst of the present invention, it is preferable to use synthesized apatites.

Among the phosphate apatites, calcium hydroxyapatite may be synthesized by the following method, but the synthesis is not limited thereto. Two types of synthesis are known, roughly classified into wet synthesis and dry synthesis. The wet synthesis methods include a method in which the apatite is precipitated from an aqueous ammonium dihydrogen phosphate solution and an aqueous calcium nitrate solution; a method in which the apatite is precipitated from calcium hydroxide and an aqueous phosphoric acid solution; and a method in which $CaHPO_4 \cdot 2H_2O$, $\alpha$-$Ca_3(PO_4)_2$, $\beta$-$Ca_3(PO_4)_2$, or $Ca_4(PO_4)_2O$ is hydrolyzed. Large crystals of apatite can be obtained by hydrothermal synthesis methods.

The apatites may be used as catalysts directly, or they may be supported on carriers.

When the apatite is used as it is, the apatite particles are shaped and pelletized. The shaping method is not particularly restricted, and standard shaping methods may be employed. Examples of the shaping methods include tumbling, extrusion and compression molding with a tablet press.

By adding other components and adjusting the shaping conditions during the shaping of the particles, it is possible to improve the strength of the catalyst. For example, by adding water while adjusting the amount thereof, it is possible to control the shape and strength of the pellets.

A binder may be used to improve the strength of the catalyst. Both inorganic and organic binders are known. Examples of the known inorganic binders include sols such as silica and alumina sols, water glass, gypsum, phosphates, water, cement, lime, and clay. Examples of the known organic binders include thermoplastic resins such as polyvinyls, polyethylenes, methacrylic resins, polystyrenes, polyesters and vinyl acetate resins, thermosetting resins such as phenolic resins and epoxy resins, natural rubbers, rubbers such as butyl, nitrile, acrylic, styrene butadiene, butadiene and chloroprene rubbers, starches, proteins, seaweeds, saccharides, natural rubbers, bitumen, and celluloses. For example, when a silica sol is used as a binder, the phosphate and the silica sol may be kneaded, granulated and dried.

In the compression molding with a tablet press, it is possible to use a matrix-type binder such as coal tar pitch, clays, waxes or paraffins, or a film-type binder such as sodium silicate or polyvinyl alcohols. Furthermore, a lubricant may be used, with examples including water, lubricating oils, talcs, magnesium stearate, glycerin, silicone, ethylene glycol, and graphite. (Reference: "Zouryuu Binran (Granulation Handbook)" Association of Powder Process Industry and Engineering, JAPAN, Ohmsha, Ltd.)

When the apatite is supported on a carrier, the carrier may be silica gel, alumina, activated carbon, etc. The method for supporting the apatite on the carrier is not particularly restricted. For example, the carrier may be impregnated with an aqueous solution or suspension of the apatite, and may then be dried and calcined. In the case of apatite poorly soluble in water, the apatite may be synthesized on the surface of the carrier to directly produce the supported apatite.

In the present invention, it is preferable to calcine the apatite prior to the reaction.

The calcination may be carried out in a standard calcining tube or muffle furnace, generally under atmospheric pressure or reduced pressure or at a superatmospheric pressure of 0.2 MPa or less, in air or in the presence of an inert gas such as nitrogen, at 100-800° C., and preferably 200-500° C.

The α,β-unsaturated ether production method of the present invention is carried out using a catalyst containing the specific apatite represented by any of general formulae (1)-(4) above. In the method, a gas-phase flow reactor having a fixed bed or a fluidized bed may be used. For example, satisfactory results may be obtained with a gas-phase flow reactor that is provided with a fixed bed formed by a catalyst having a 10-20 mesh particle size. The fixed bed reaction tube may be a vertical tube or a horizontal tube.

The temperature of the gas-phase acetal thermolysis reaction may differ depending on the type of raw material acetal and the contact time with the catalyst, but is preferably in the range of 150-400° C., and particularly 200-380° C. The temperature above the lower limit ensures that the equilibrium is shifted such that the raw material acetal is converted to a sufficiently high degree. The temperature below the upper limit ensures that side reactions hardly occur and coke deposition does not increase. Continuous operation is possible by sequentially introducing the raw material acetal while maintaining the reaction zone at a specified reaction temperature. In this case, the acetal is preferably preheated.

Moreover, the pressure during the reaction may be atmospheric pressure, reduced pressure or superatmospheric pressure. But the reaction is preferably carried out at atmospheric pressure or below in terms of equilibrium reaction.

To isolate the target α,β-unsaturated ether from the product from the catalyzed thermolysis, the gaseous mixture emitted from the reactor may be subjected to fractional distillation.

EXAMPLES

Herebelow, preferred embodiments of the present invention will be described in greater detail by examples, but the present invention is by no means limited to these examples.

In Examples, the conversion of acetal, the selectivity and yield of vinyl ether, and the selectivity for acetaldehyde are defined by the following formulae.

Acetal conversion (%)=((number of moles of reacted acetal)/(number of moles of acetal supplied to the reaction))×100

Vinyl ether selectivity (%)=((number of moles of vinyl ether produced)/(number of moles of reacted acetal))×100

Vinyl ether yield (%)=((acetal conversion (%))×(vinyl ether selectivity (%))/100

Acetaldehyde selectivity (%) ((number of moles of acetaldehyde produced)/(number of moles of reacted acetal))×100

Moreover, the following physical properties were measured.

[Elemental Analysis]

Several mg to over 10 mg of a sample was weighed out and dissolved (decomposed) in hydrochloric acid at room temperature. Thereafter, the volume was made up to 250 ml, Ca and P were determined by ICP emission spectrometry, and the concentrations thereof in the sample were calculated. The ICP spectrometer was ICPS-8000E from Shimadzu Corporation.

[X-ray Powder Diffraction (XRD)]

A sample crushed in an agate mortar was packed into a dedicated glass plate having a groove 0.5 mm in depth, and was analyzed under the following measurement conditions.

The diffractometer was MXP18VAHF from Bruker aXS.

Measurement Conditions
X-ray generator: 18 kW (400 mA)
Radiation source: Cu
Wavelength: 1.54056 Å
Goniometer: vertical
Tube voltage: 50.0 kV
Tube current: 180.0 mA
Data range: 10-90 deg

[Hammett acidity ($H_0$)]

5-10 $cm^3$ of benzene was placed in a 50 $cm^3$ Erlenmeyer flask, and a small quantity of powdered sample was quickly added. Next, approximately 0.1 $cm^3$ each of indicator solutions were added sequentially in order of increasing pKa, and the maximum acid strength was determined from the pKa of the indicator that first showed an acid color.

[Infrared Absorption Spectroscopy (FT-IR)]

A sample was powdered in an agate mortar, and was packed into a diffusion-type FT-IR spectrometer (Nocolet 6700 FT-IR, Thermo Electron Corp.). The temperature was increased to 350° C. at 10° C./min under a stream of nitrogen and then held constant for 30 minutes to remove the moisture physically adsorbed on the sample. The temperature was returned to ambient and the sample was subjected to infrared absorption spectroscopy.

[ASAP Measurement]

The BET specific surface area was measured under the following conditions.

The apparatus was Micromerics ASAP2000 from Shimadzu Corporation.

Measurement conditions: Nitrogen adsorption method, Temperature 77K, BJH Desorption

Example 1

Catalyst preparation: 10 g of hydroxy apatite $Ca_5(PO_4)_3$ (OH) (Wako Pure Chemical Industries, Ltd.) was pressure molded at a pressure of 20 MPa for 5 minutes to give granules having diameters of 0.5-1.0 mm. The granules were placed in a calcining tube, then calcined under nitrogen for 3 hours at atmospheric pressure at 350° C., and cooled to ambient temperature in 1 hour in a nitrogen flow. A catalyst was thus prepared.

Reaction experiment: 1 mL of the catalyst prepared as above was packed into a stainless steel reaction tube having a diameter of 12.7 mm. Raw material acetaldehyde diethyl acetal was fed to the reaction tube at a rate of 3.7 g/h, vaporized at 250° C., and allowed to react at 220° C. at atmospheric pressure.

6 hours after the start of the reaction, the reaction liquid was analyzed by gas chromatography, with the results confirming that ethyl vinyl ether was the primary product, and that the acetal conversion was 46.5%, the vinyl ether selectivity was 91.4%, and the vinyl ether yield was 42.5%. The results are shown in Table 3.

Example 2

Catalyst preparation: 10 g of fluoroapatite $Ca_5(PO_4)_3$ (F) (Wako Pure Chemical Industries, Ltd.) was pressure molded at a pressure of 20 MPa for 5 minutes to give granules having diameters of 0.5-11.0 mm. The granules were placed in a calcining tube, then calcined under nitrogen for 3 hours at atmospheric pressure at 350° C., and cooled to ambient temperature in 1 hour in a nitrogen flow. A catalyst was thus prepared.

Reaction experiment: 1 mL of the catalyst prepared as above was packed into a stainless steel reaction tube having a diameter of 12.7 mm. Raw material acetaldehyde diethyl acetal was fed to the reaction tube at a rate of 3.7 g/h, vaporized at 250° C., and allowed to react at 220° C. at atmospheric pressure.

6 hours after the start of the reaction, the reaction liquid was analyzed by gas chromatography, with the results confirming that ethyl vinyl ether was the primary product, and that the acetal conversion was 49.6%, the vinyl ether selectivity was 92.6%, and the vinyl ether yield was 45.9%.

The results are shown in Table 3.

Comparative Example 1

Catalyst preparation: 10 g of lithium phosphate (Junsei Chemical Co., Ltd.) was pressure molded at a pressure of 20 MPa for 5 minutes to give granules having diameters of 0.5-1.0 mm. The granules were placed in a calcining tube, then calcined under nitrogen for 3 hours at atmospheric pressure and 350° C., and cooled to ambient temperature in 1 hour in a nitrogen flow. A catalyst was thus prepared.

Reaction experiment: 1 mL of the catalyst prepared as above was packed into a stainless steel reaction tube having a diameter of 12.7 mm. Raw material acetaldehyde diethyl acetal was fed to the reaction tube at a rate of 3.7 g/h, vaporized at 250° C., and allowed to react at 220° C. at atmospheric pressure.

0.5 hour after the start of the reaction, the reaction liquid was analyzed by gas chromatography, with the results confirming that ethyl vinyl ether was the primary product, and that the acetal conversion was 40.8%, the vinyl ether selectivity was 71.6%, and the vinyl ether yield was 29.2%. The results are shown in Table 3.

Comparative Example 2

Catalyst preparation: 10 g of calcium sulfate (Junsei Chemical Co., Ltd.) was pressure molded at a pressure of 20 MPa for 5 minutes to give granules having diameters of 0.5-1.0 mm. The granules were placed in a calcining tube, then calcined under nitrogen for 3 hours at atmospheric pressure and 350° C., and cooled to ambient temperature in 1 hour in a nitrogen flow. A catalyst was thus prepared.

Reaction experiment: 1 mL of the catalyst prepared as above was packed into a stainless steel reaction tube having a diameter of 12.7 mm. Raw material acetaldehyde diethyl acetal was fed to the reaction tube at a rate of 3.7 g/h, vaporized at 250° C., and allowed to react at 220° C. at atmospheric pressure.

6 hours after the start of the reaction, the reaction liquid was analyzed by gas chromatography, with the results confirming that ethyl vinyl ether was the primary product, and that the acetal conversion was 50.6%, the vinyl ether selectivity was 79.9%, and the vinyl ether yield was 40.5%.

The results are shown in Table 3.

TABLE 3

|  | Acetal conversion (%) | Vinyl ether selectivity (%) | Vinyl ether yield (%) |
| --- | --- | --- | --- |
| Example 1 | 46.5 | 91.4 | 42.5 |
| Example 2 | 49.6 | 92.6 | 45.9 |
| Comparative Example 1 | 40.8 | 71.6 | 29.2 |
| Comparative Example 2 | 50.6 | 79.9 | 40.5 |

It was understood from Table 3 that Examples 1 and 2 resulted in improved vinyl ether selectivity and vinyl ether yield compared to Comparative Examples 1 and 2.

Example 3

Catalyst preparation: 50 g of hydroxy apatite $Ca_5(PO_4)_3(OH)$ (Junsei Chemical Co., Ltd.) was pressure molded at a pressure of 20 MPa for 5 minutes to give granules having diameters of 10-20 mesh. The granules were placed in a calcining tube, then calcined under nitrogen for 3 hours at atmospheric pressure at 350° C., and cooled to ambient temperature in 1 hour in a nitrogen flow. A catalyst was thus prepared.

Reaction experiment: 10 mL of the catalyst prepared as above was packed into a stainless steel reaction tube having a diameter of 23 mm. Raw material acetaldehyde diethyl acetal was fed to the reaction tube at a rate of 35 g/h, vaporized at 250° C., and allowed to react at 330° C. at atmospheric pressure.

5 hours after the start of the reaction, the reaction liquid was analyzed by gas chromatography, with the results confirming that ethyl vinyl ether was the primary product, and that the acetal conversion was 98.6%, the vinyl ether selectivity was 97.5%, and the vinyl ether yield was 96.1%.

The results are shown in Table 4.

Comparative Example 3

Catalyst preparation: 50 g of calcium sulfate (Junsei Chemical Co., Ltd.) was pressure molded at a pressure of 20 MPa for 5 minutes to give granules having diameters of 10-20 mesh. The granules were placed in a calcining tube, then calcined under nitrogen for 3 hours at atmospheric pressure and 350° C., and cooled to ambient temperature in 1 hour in a nitrogen flow. A catalyst was thus prepared.

Reaction experiment: 10 mL of the catalyst prepared as above was packed into a stainless steel reaction tube having a diameter of 23 mm. Raw material acetaldehyde diethyl acetal was fed to the reaction tube at a rate of 35 g/h, vaporized at 250° C., and allowed to react at 330° C. at atmospheric pressure.

5 hours after the start of the reaction, the reaction liquid was analyzed by gas chromatography, with the results confirming that ethyl vinyl ether was the primary product, and that the acetal conversion was 98.7%, the vinyl ether selectivity was 92.2%, and the vinyl ether yield was 91.0%.

The results are shown in Table 4.

TABLE 4

|  | Acetal conversion (%) | Vinyl ether selectivity (%) | Vinyl ether yield (%) |
| --- | --- | --- | --- |
| Example 3 | 98.6 | 97.5 | 96.1 |
| Comparative Example 3 | 98.7 | 92.2 | 91.0 |

It was understood from Table 4 that Example 3 resulted in improved vinyl ether selectivity and vinyl ether yield compared to Comparative Example 3.

Example 4

Catalyst preparation: 10 g of hydroxy apatite $Ca_5(PO_4)_3$(OH) (purchased from Junsei Chemical Co., Ltd.) was pressure molded at a pressure of 20 MPa for 5 minutes to give granules having diameters of 0.5-1.0 mm. The granules were placed in a calcining tube, then calcined under nitrogen for 3 hours at atmospheric pressure at 350° C., and cooled to ambient temperature in 1 hour in a nitrogen flow. A catalyst was thus prepared.

According to the elemental analysis with the obtained catalyst, the content of Ca was 38.4 wt. %, the content of P was 17.7 wt. %, and the Ca/P ratio was 1.7, which was consistent with the theoretical Ca/P ratio of the hydroxyapatite $Ca_5(PO_4)_3$ (OH).

The Hammett acidity was measured to be $4.0<H_0\leq4.8$.

The BET specific surface area was measured to be 57.8 $m^2/g$.

The results of X-ray powder diffraction measurement are shown in FIG. 1. It was understood that these were consistent with a hydroxyapatite diffraction pattern.

Reaction experiment: 1 mL of the catalyst prepared as above was packed into a stainless steel reaction tube having a diameter of 12.7 mm. Raw material acetaldehyde diethyl acetal was fed to the reaction tube at a rate of 3.7 g/h, vaporized at 250° C., and allowed to react at 220° C. at atmospheric pressure.

6 hours after the start of the reaction, the reaction liquid was analyzed by gas chromatography, with the results confirming that ethyl vinyl ether was the primary product, and that the acetal conversion was 63.1%, the vinyl ether selectivity was 96.6%, and the vinyl ether yield was 61.0%. Separately, the reaction was performed at an elevated temperature of 350° C., and the reaction liquid was analyzed after 6 hours, resulting in an acetal conversion of 97.8%, an ethyl vinyl ether selectivity of 96.0%, and a selectivity for acetaldehyde (side product) of 2.5%. The results are shown in Table 5.

Example 5

Catalyst preparation: 10 g of hydroxy apatite $Ca_5 (PO_4)_3$ (OH) (HAP manufactured by Wako Pure Chemical Industries, Ltd., crystalline, biomaterial research grade) was pressure molded at a pressure of 20 MPa for 5 minutes to give granules having diameters of 0.5-1.0 mm. The granules were placed in a calcining tube, then calcined under nitrogen for 3 hours at atmospheric pressure at 350° C., and cooled to ambient temperature in 1 hour in a nitrogen flow. A catalyst was thus prepared.

According to the elemental analysis with the obtained catalyst, the content of Ca was 38.2 wt. %, the content of P was 17.3 wt. %, and the Ca/P ratio was 1.7, which was consistent with the theoretical Ca/P ratio of the hydroxyapatite $Ca_5(PO_4)_3$(OH).

The Hammett acidity was measured to be $4.0<H_0\leq4.8$.

The BET specific surface area was measured to be 10.5 $m^2/g$.

The results of X-ray powder diffraction measurement are shown in FIG. 2. It was understood that these were consistent with a hydroxyapatite diffraction pattern.

Reaction experiment: 1 mL of the catalyst prepared as above was packed into a stainless steel reaction tube having a diameter of 12.7 mm. Raw material acetaldehyde diethyl acetal was fed to the reaction tube at a rate of 3.7 g/h, vaporized at 250° C., and allowed to react at 220° C. at atmospheric pressure.

6 hours after the start of the reaction, the reaction liquid was analyzed by gas chromatography, with the results confirming that ethyl vinyl ether was the primary product, and that the acetal conversion was 46.5%, the vinyl ether selectivity was 91.4%, and the vinyl ether yield was 42.5%. Separately, the reaction was performed at an elevated temperature of 350° C., and the reaction liquid was analyzed after 6 hours, resulting in an acetal conversion of 98.3%, an ethyl vinyl ether selectivity of 97.0%, and a selectivity for acetaldehyde (side product) of 2.4%. The results are shown in Table 5.

Example 6

Catalyst preparation: 10 g of fluoroapatite $Ca_5(PO_4)_3(F)$ (FAP manufactured by Wako Pure Chemical Industries, Ltd., crystalline, biomaterial research grade) was pressure molded at a pressure of 20 MPa for 5 minutes to give granules having diameters of 0.5-1.0 mm. The granules were placed in a calcining tube, then calcined under nitrogen for 3 hours at atmospheric pressure at 350° C., and cooled to ambient temperature in 1 hour in a nitrogen flow. A catalyst was thus prepared.

The Hammett acidity was measured to be $4.0<H_0\leq4.8$.

The results of X-ray powder diffraction measurement are shown in FIG. 3. It was understood that these were consistent with a fluoroapatite diffraction pattern, and were similar to a hydroxyapatite diffraction pattern due to the similarities in apatite structures.

Reaction experiment: 1 mL of the catalyst prepared as above was packed into a stainless steel reaction tube having a diameter of 12.7 mm. Raw material acetaldehyde diethyl acetal was fed to the reaction tube at a rate of 3.7 g/h, vaporized at 250° C., and allowed to react at 220° C. at atmospheric pressure.

6 hours after the start of the reaction, the reaction liquid was analyzed by gas chromatography, with the results confirming that ethyl vinyl ether was the primary product, and that the acetal conversion was 49.6%, the vinyl ether selectivity was 92.6%, and the vinyl ether yield was 45.9%. Separately, the reaction was performed at an elevated temperature of 350° C., and the reaction liquid was analyzed after 6 hours, resulting in an acetal conversion of 98.3%, an ethyl vinyl ether selectivity of 97.0%, and a selectivity for acetaldehyde (side product) of 2.4%. The results are shown in Table 5.

Comparative Example 4

Catalyst preparation: 10 g of calcium hydrogen phosphate $CaHPO_4$ was pressure molded at a pressure of 20 MPa for 5 minutes to give granules having diameters of 0.5-1.0 mm. The granules were placed in a calcining tube, then calcined under nitrogen for 3 hours at atmospheric pressure and 350° C., and cooled to ambient temperature in 1 hour in a nitrogen flow. A catalyst was thus prepared.

Reaction experiment: 1 mL of the catalyst prepared as above was packed into a stainless steel reaction tube having a diameter of 12.7 mm. Raw material acetaldehyde diethyl acetal was fed to the reaction tube at a rate of 3.7 g/h, vaporized at 250° C., and allowed to react at 220° C. at atmospheric pressure.

6 hours after the start of the reaction, the reaction liquid was analyzed by gas chromatography, with the results confirming that ethyl vinyl ether was the primary product, and that the acetal conversion was 71.7%, the vinyl ether selectivity was 98.8%, and the vinyl ether yield was 70.8%. Separately, the reaction was performed at an elevated temperature of 350° C., and the reaction liquid was analyzed after 6 hours, resulting in an acetal conversion of 97.2%, an ethyl vinyl ether selectivity of 92.6%, and a selectivity for acetaldehyde (side product) of 5.5%. As shown above, increasing the reaction temperature in an attempt to increase the conversion resulted in a lower selectivity for the ethyl vinyl ether and increased by-production of acetaldehyde, in contrast to the results with the apatite catalyst systems. The results are shown in Table 5.

Comparative Example 5

Catalyst preparation: 10 g of aluminum phosphate $AlPO_4$ was pressure molded at a pressure of 20 MPa for 5 minutes to give granules having diameters of 0.5-1.0 mm. The granules were placed in a calcining tube, then calcined under nitrogen for 3 hours at atmospheric pressure and 350° C., and cooled to ambient temperature in 1 hour in a nitrogen flow. A catalyst was thus prepared.

Reaction experiment: 1 mL of the catalyst prepared as above was packed into a stainless steel reaction tube having a diameter of 12.7 mm. Raw material acetaldehyde diethyl acetal was fed to the reaction tube at a rate of 3.7 g/h, vaporized at 250° C., and allowed to react at 220° C. at atmospheric pressure.

6 hours after the start of the reaction, the reaction liquid was analyzed by gas chromatography, with the results confirming that ethyl vinyl ether was the primary product, and that the acetal conversion was 47.7%, the vinyl ether selectivity was 90.2%, and the vinyl ether yield was 43.0%. Separately, the reaction was performed at an elevated temperature of 350° C., and the reaction liquid was analyzed after 6 hours, resulting in an acetal conversion of 88.2%, an ethyl vinyl ether selectivity of 95.1%, and a selectivity for acetaldehyde (side product) of 3.7%. From the results, it was understood that the increase in conversion by raising the temperature was smaller than with the apatite catalyst systems. The results are shown in Table 5.

Comparative Example 6

Catalyst preparation: 10 g of α-calcium phosphate $Ca_3(PO_4)_2$ was pressure molded at a pressure of 20 MPa for 5 minutes to give granules having diameters of 0.5-1.0 mm. The granules were placed in a calcining tube, then calcined under nitrogen for 3 hours at atmospheric pressure at 350° C., and cooled to ambient temperature in 1 hour in a nitrogen flow. A catalyst was thus prepared.

The Hammett acidity was measured to be $4.0 < H_0 \leq 4.8$.

The results of X-ray powder diffraction measurement are shown in FIG. 4. It was understood that these differed from the diffraction pattern of apatite structure, and that the crystalline structure was different from that of apatites.

Reaction experiment: 1 mL of the catalyst prepared as above was packed into a stainless steel reaction tube having a diameter of 12.7 mm. Raw material acetaldehyde diethyl acetal was fed to the reaction tube at a rate of 3.7 g/h, vaporized at 250° C., and allowed to react at 350° C. at atmospheric pressure.

6 hours after the start of the reaction, the reaction liquid was analyzed by gas chromatography, with the results confirming that ethyl vinyl ether was the primary product, and that the acetal conversion was 28.0%, the ethyl vinyl ether selectivity was 94.9%, and the selectivity for acetaldehyde (side product) was 3.6%. The results are shown in Table 5.

Comparative Example 7

Catalyst preparation: 10 g of β-calcium phosphate $Ca_3(PO_4)_2$ was pressure molded at a pressure of 20 MPa for 5 minutes to give granules having diameters of 0.5-1.0 mm. The granules were placed in a calcining tube, then calcined under nitrogen for 3 hours at atmospheric pressure at 350° C., and cooled to ambient temperature in 1 hour in a nitrogen flow. A catalyst was thus prepared.

The Hammett acidity was measured to be $4.8 < H_0$.

The results of X-ray powder diffraction measurement are shown in FIG. 5. As with the $α-Ca_3(PO_4)_2$, it was understood that these differed from the diffraction pattern of apatite structure, and that the crystalline structure was different from that of apatites.

Reaction experiment: 1 mL of the catalyst prepared as above was packed into a stainless steel reaction tube having a diameter of 12.7 mm. Raw material acetaldehyde diethyl acetal was fed to the reaction tube at a rate of 3.7 g/h, vaporized at 250° C., and allowed to react at 350° C. at atmospheric pressure.

6 hours after the start of the reaction, the reaction liquid was analyzed by gas chromatography, with the results confirming that ethyl vinyl ether was the primary product, and that the acetal conversion was 10.2%, the ethyl vinyl ether selectivity was 87.9%, and the selectivity for acetaldehyde (side product) was 8.5%.

The results are shown in Table 5.

Comparative Example 8

Catalyst preparation: 10 g of tetracalcium phosphate $Ca_4(PO_4)_2O$ was pressure molded at a pressure of 20 MPa for 5 minutes to give granules having diameters of 0.5-1.0 mm. The granules were placed in a calcining tube, then calcined under nitrogen for 3 hours at atmospheric pressure at 350° C., and cooled to ambient temperature in 1 hour in a nitrogen flow. A catalyst was thus prepared.

The Hammett acidity was measured to be $4.8 < H_0$.

The results of X-ray powder diffraction measurement are shown in FIG. 6. It was understood that the crystalline structure was different from that of apatites.

Reaction experiment: 1 mL of the catalyst prepared as above was packed into a stainless steel reaction tube having a diameter of 12.7 mm. Raw material acetaldehyde diethyl acetal was fed to the reaction tube at a rate of 3.7 g/h, vaporized at 250° C., and allowed to react at 350° C. at atmospheric pressure.

6 hours after the start of the reaction, the reaction liquid was analyzed by gas chromatography, with the results confirming that ethyl vinyl ether was the primary product, and that the acetal conversion was 3.5%, the ethyl vinyl ether selectivity was 72.2%, and the selectivity for acetaldehyde (side product) was 18.1%.

The results are shown in Table 5.

Comparative Example 9

Catalyst preparation: 10 g of calcium pyrophosphate $Ca_2P_2O_7$ was pressure molded at a pressure of 20 MPa for 5 minutes to give granules having diameters of 0.5-1.0 mm. The granules were placed in a calcining tube, then calcined under nitrogen for 3 hours at atmospheric pressure at 350° C., and cooled to ambient temperature in 1 hour in a nitrogen flow. A catalyst was thus prepared.

Reaction experiment: 1 mL of the catalyst prepared as above was packed into a stainless steel reaction tube having a diameter of 12.7 mm. Raw material acetaldehyde diethyl acetal was fed to the reaction tube at a rate of 3.7 g/h, vaporized at 250° C., and allowed to react at 350° C. at atmospheric pressure.

6 hours after the start of the reaction, the reaction liquid was analyzed by gas chromatography, with the results confirming that ethyl vinyl ether was the primary product, and that the acetal conversion was 62.6%, the ethyl vinyl ether selectivity was 97.6%, and the selectivity for acetaldehyde (side product) was 1.7%.

The results are shown in Table 5.

Comparative Example 10

Catalyst preparation: 10 g of magnesium phosphate octahydrate (Junsei Chemical Co., Ltd.) was pressure molded at a pressure of 20 MPa for 5 minutes to give granules having diameters of 0.5-1.0 mm. The granules were placed in a calcining tube, then calcined under nitrogen for 3 hours at atmospheric pressure and 350° C., and cooled to ambient temperature in 1 hour in a nitrogen flow. A catalyst was thus prepared.

Reaction experiment: 1 mL of the catalyst prepared as above was packed into a stainless steel reaction tube having a diameter of 12.7 mm. Raw material acetaldehyde diethyl acetal was fed to the reaction tube at a rate of 3.7 g/h, vaporized at 250° C., and allowed to react at 350° C. at atmospheric pressure.

6 hours after the start of the reaction, the reaction liquid was analyzed by gas chromatography, with the results confirming that ethyl vinyl ether was the primary product, and that the acetal conversion was 99.1%, the ethyl vinyl ether selectivity was 90.4%, and the selectivity for acetaldehyde (side product) was 7.6%.

The results are shown in Table 5. It was understood that more acetaldehyde was by-produced as compared to the reactions with the apatite catalysts.

Example 7

A reaction was carried out under the following conditions using the hydroxyapatite $Ca_5(PO_4)_3$ (OH) prepared in Example 4 as a catalyst.

Reaction experiment: 10 mL of the catalyst prepared as above was packed into a stainless steel reaction tube having a diameter of 23 mm. Raw material acetaldehyde diethyl acetal was fed to the reaction tube at a rate of 35 g/h, vaporized at 250° C., and allowed to react at 330° C. at atmospheric pressure.

5 hours after the start of the reaction, the reaction liquid was analyzed by gas chromatography, with the results confirming that ethyl vinyl ether was the primary product, and that the acetal conversion was 98.5%, the vinyl ether selectivity was 96.7%, and the selectivity for acetaldehyde (side product) was 2.7%.

The results are shown in Table 6.

Example 8

A reaction was carried out under the following conditions using the hydroxyapatite $Ca_5(PO_4)_3(OH)$ prepared in Example 5 as a catalyst.

Reaction experiment: 10 mL of the catalyst prepared as above was packed into a stainless steel reaction tube having a diameter of 23 mm. Raw material acetaldehyde diethyl acetal was fed to this reaction tube at a rate of 35 g/h, vaporized at 250° C., and allowed to react at 330° C. at atmospheric pressure.

5 hours after the start of the reaction, the reaction liquid was analyzed by gas chromatography, with the results confirming that ethyl vinyl ether was the primary product, and that the acetal conversion was 98.6%, the vinyl ether selectivity was 97.5%, and the selectivity for acetaldehyde (side product) was 2.5%.

The results are shown in Table 6.

Example 9

A reaction was carried out under the following conditions using the fluoroapatite $Ca_5(PO_4)_3(F)$ prepared in Example 6 as a catalyst.

TABLE 5

| | | Reaction temperature = 220° C. | | Reaction temperature = 350° C. | | |
|---|---|---|---|---|---|---|
| | Catalyst | Acetal conversion (%) | Vinyl ether selectivity (%) | Acetal conversion (%) | Vinyl ether selectivity (%) | Acetaldehyde selectivity (%) |
| Ex. 4 | $Ca_5(PO_4)_3(OH)$ | 63.1 | 96.6 | 97.8 | 96.0 | 2.5 |
| Ex. 5 | $Ca_5(PO_4)_3(OH)$ | 46.5 | 91.4 | 98.3 | 97.0 | 2.4 |
| Ex. 6 | $Ca_5(PO_4)_3(F)$ | 49.6 | 92.6 | 98.3 | 97.0 | 2.4 |
| Comp. Ex. 4 | $CaHPO_4$ | 71.7 | 98.8 | 97.2 | 92.6 | 5.5 |
| Comp. Ex. 5 | $AlPO_4$ | 47.7 | 90.2 | 88.2 | 95.1 | 3.7 |
| Comp. Ex. 6 | $\alpha\text{-}Ca_3(PO_4)_2$ | — | — | 28.0 | 94.9 | 3.6 |
| Comp. Ex. 7 | $\beta\text{-}Ca_3(PO_4)_2$ | — | — | 10.2 | 87.9 | 8.5 |
| Comp. Ex. 8 | $Ca_4(PO_4)_2O$ | — | — | 3.5 | 72.2 | 18.1 |
| Comp. Ex. 9 | $Ca_2P_2O_7$ | — | — | 62.6 | 97.6 | 1.7 |
| Comp. Ex. 10 | $Mg_3(PO_4)_2$ | — | — | 99.1 | 90.4 | 7.6 |

Reaction experiment: 10 mL of the catalyst prepared as above was packed into a stainless steel reaction tube having a diameter of 23 mm. Raw material acetaldehyde diethyl acetal was fed to the reaction tube at a rate of 35 g/h, vaporized at 250° C., and allowed to react at 330° C. at atmospheric pressure.

5 hours after the start of the reaction, the reaction liquid was analyzed by gas chromatography, with the results confirming that ethyl vinyl ether was the primary product, and that the acetal conversion was 98.4%, the vinyl ether selectivity was 97.7%, and the selectivity for acetaldehyde (side product) was 2.1%.

The results are shown in Table 6.

Example 10

5 g of fumed silica (CABOSIL M-5) was added to 45 g of hydroxyapatite $Ca_5(PO_4)_3(OH)$, and the mixture was pressure molded at a pressure of 20 MPa for 5 minutes to give granules having diameters of 0.5-1.0 mm. The granules were placed in a calcining tube, then calcined under nitrogen for 3 hours at atmospheric pressure at 350° C., and cooled to ambient temperature in 1 hour in a nitrogen flow. A catalyst was thus prepared.

Reaction experiment: 10 mL of the catalyst prepared as above was packed into a stainless steel reaction tube having a diameter of 23 mm. Raw material acetaldehyde diethyl acetal was fed to the reaction tube at a rate of 35 g/h, vaporized at 250° C., and allowed to react at 330° C. at atmospheric pressure.

5 hours after the start of the reaction, the reaction liquid was analyzed by gas chromatography, with the results confirming that ethyl vinyl ether was the primary product, and that the acetal conversion was 98.5%, the vinyl ether selectivity was 97.3%, and the selectivity for acetaldehyde (side product) was 2.6%.

The results are shown in Table 6.

Comparative Example 11

Catalyst preparation: 50 g of calcium sulfate (calcined gypsum) was pressure molded at a pressure of 20 MPa for 5 minutes to give granules having diameters of 10-20 mesh. The granules were placed in a calcining tube, then calcined under nitrogen for 3 hours at atmospheric pressure and 350° C., and cooled to ambient temperature in 1 hour in a nitrogen flow. A catalyst was thus prepared.

Reaction experiment: 10 mL of the catalyst prepared as above was packed into a stainless steel reaction tube having a diameter of 23 mm. Raw material acetaldehyde diethyl acetal was fed to the reaction tube at a rate of 35 g/h, vaporized at 250° C., and allowed to react at 330° C. at atmospheric pressure.

5 hours after the start of the reaction, the reaction liquid was analyzed by gas chromatography, with the results confirming that ethyl vinyl ether was the primary product, and that the acetal conversion was 98.7%, the vinyl ether selectivity was 92.2%, and the selectivity for acetaldehyde (side product) was 6.9%.

It was understood that more acetaldehyde was by-produced than with the apatite catalysts. The results are shown in Table 6.

TABLE 6

| | Catalyst | Acetal conversion (%) | Vinyl ether selectivity (%) | Acetaldehyde selectivity (%) |
|---|---|---|---|---|
| Example 7 | $Ca_5(PO_4)_3(OH)$ | 98.5 | 96.7 | 2.7 |
| Example 8 | $Ca_5(PO_4)_3(OH)$ | 98.6 | 97.5 | 2.5 |
| Example 9 | $Ca_5(PO_4)_3(F)$ | 98.4 | 97.7 | 2.1 |
| Example 10 | $Ca_5(PO_4)_3(OH)/SiO_2$ | 98.5 | 97.3 | 2.6 |
| Comparative Example 11 | $CaSO_4$ | 98.7 | 92.2 | 6.9 |

Example 11

The following continuous reaction experiment was carried out using the hydroxyapatite $Ca_5(PO_4)_3(OH)$ prepared in Example 4 as a catalyst.

Reaction experiment: 2 mL of the catalyst prepared in Example 4 was packed into a stainless steel reaction tube having a diameter of 12.7 mm. Raw material acetaldehyde diethyl acetal was fed to the reaction tube at a rate of 0.2 mL/min, vaporized at 300° C., and allowed to react at 310° C. at atmospheric pressure.

The reaction time and reaction results are shown in Table 7. It was understood that the acetal conversion or vinyl ether selectivity did not substantially decrease during the reaction for 1008 hours.

TABLE 7

| Reaction time | Acetal conversion (%) | Vinyl ether selectivity (%) |
|---|---|---|
| 47 h | 96.0 | 96.8 |
| 504 h | 97.9 | 96.1 |
| 1008 h | 97.7 | 96.0 |

Example 12

Catalyst preparation: 50 g of calcium hydroxide was suspended in 5 L of water, and an aqueous phosphoric acid solution was added dropwise to this suspension over a period of 12 hours while keeping the solution in an alkaline state at a pH of 11 or higher. After the dropwise addition was complete, the suspension was agitated for another 12 hours at ambient temperature. Thereafter, the entire suspension was filtered, and the filtered white solid was suspended again in 4 L of water and agitated for 12 hours at ambient temperature. The white suspension was filtered again, and the filtered white solid was dried at 100° C. for 24 hours. The results of X-ray powder diffraction measurement for the white solid obtained are shown in FIG. 7. An apatite structure was confirmed. The yield of the white solid was 56 g, which represented a 98% yield from the raw material calcium hydroxide.

10 g of the apatite obtained by above-mentioned preparation was pressure molded at a pressure of 20 MPa for 5 minutes to give granules having diameters of 10-20 mesh. The granules were placed in a calcining tube, then calcined under nitrogen for 3 hours at atmospheric pressure and 350° C., and cooled to ambient temperature in 1 hour in a nitrogen flow. A catalyst was thus prepared. The catalyst was subjected to FT-IR analysis, and absorption peaks were observed at 3572 cm$^{-1}$ due to the —OH groups characteristic in the apatite structure, and at 1460 cm$^{-1}$ and 1420 cm$^{-1}$ which were characteristic of the $CO_3^{2-}$ group substituted at the $PO_4$ site in the apatite structure (Muki Material (Inorganic Materials), Vol. 5, Sep. 398-404 (1998)). The FT-IR analysis results are shown in FIG. 8.

Reaction experiment: 10 mL of the catalyst prepared as above was packed into a stainless steel reaction tube having a diameter of 23 mm. Raw material acetaldehyde diethyl acetal was fed to the reaction tube at a rate of 35 g/h, vaporized at 250° C., and allowed to react at 330° C. at atmospheric pressure. 6.5 hours after the start of the reaction, the reaction liquid was analyzed by gas chromatography, with the results confirming that ethyl vinyl ether was the primary product, and that the acetal conversion was 97.3%, the vinyl ether selectivity was 97.5%, and the vinyl ether yield was 94.9%.

Example 13

Catalyst preparation: 250 g of water was added to 400 g of hydroxyapatite powder (Junsei Chemical Co., Ltd.) and these were kneaded sufficiently. The material was extruded through an extruder (screw type, axial extrusion, manufactured by Honda Tekko, 3.2φ die), cut to a length of 3-7 mm, and dried at 110° C. for 12 hours. Furthermore, the pellets were calcined at 350° C. under a stream of nitrogen for 3 hours. The resultant catalyst was crushed and selected to have particle diameters of 10-20 mesh.

Reaction experiment: 10 mL of the catalyst prepared as above was packed into a stainless steel reaction tube having a diameter of 23 mm. Raw material acetaldehyde diethyl acetal was fed to the reaction tube at a rate of 35 g/h, vaporized at 250° C., and allowed to react at 330° C. at atmospheric pressure. 5 hours after the start of the reaction, the reaction liquid was analyzed by gas chromatography, with the results confirming that ethyl vinyl ether was the primary product, and that the acetal conversion was 98.5%, the vinyl ether selectivity was 97.0%, and the vinyl ether yield was 95.6%.

Example 14

A catalyst was prepared in the same way as in Example 13 except that the calcination temperature was 400° C. A reaction experiment was carried out under the same conditions as in Example 13, and it was confirmed that ethyl vinyl ether was the primary product, and that the acetal conversion was 98.7%, the vinyl ether selectivity was 97.0%, and the vinyl ether yield was 95.7%.

Comparative Example 12

Test Results for $CaHPO_4$ Life

The following continuous reaction experiment was carried out using the calcium hydrogen phosphate catalyst prepared in Comparative Example 4.

Reaction experiment: 2 mL of the catalyst prepared in Comparative Example 4 was packed into a stainless steel reaction tube having a diameter of 12.7 mm. Raw material acetaldehyde diethyl acetal was fed to the reaction tube at a rate of 0.2 mL/min, vaporized at 300° C., and allowed to react at 300° C. at atmospheric pressure. After 10 hours, the acetal conversion was 94.4% and the vinyl ether selectivity was 96.7%. After 87 hours, the acetal conversion was 88.7% and the vinyl ether selectivity was 96.5%.

The invention claimed is:

1. A method for producing an α,β-unsaturated ether comprising thermally decomposing an acetal in the presence of a catalyst containing an apatite, the apatite being represented by general formula (1):

$$(M)_{5-y}(HZO_4)_y(ZO_4)_{3-y}(X)_{1-y} \qquad (1)$$

wherein M is at least one selected from the group consisting of Mg, Ca, Sr, Ba, Pb, Mn and Cd, Z is at least one selected from the group consisting of P, As and Sb, X is at least one selected from the group consisting of OH, F, Cl, Br, I and At, and 0≦y<1.

2. A method for producing an α,β-unsaturated ether comprising thermally decomposing an acetal in the presence of a catalyst containing a phosphate apatite, the apatite being represented by general formula (2):

$$(M)_{5-y}(HPO_4)_y(PO_4)_{3-y}(X)_{1-y} \qquad (2)$$

wherein M is at least one selected from the group consisting of Mg, Ca, Sr, Ba, Pb, Mn and Cd, X is at least one selected from the group consisting of OH, F, Cl, Br, I and At, and 0≦y<1.

3. A method for producing an α,β-unsaturated ether comprising thermally decomposing an acetal in the presence of a catalyst containing an apatite, the apatite being represented by general formula (3) or (4):

$$(M)_{5-y+2n}(HZO_4)_y(ZO_4)_{3-y}(X)_{1-y}(SiO_4)_n \qquad (3)$$

$$(M)_{5-y+m}(HZO_4)_y(ZO_4)_{3-y}(X)_{1-y}(CO_3)_m \qquad (4)$$

wherein M is at least one selected from the group consisting of Mg, Ca, Sr, Ba, Pb, Mn and Cd, Z is at least one selected from the group consisting of P, As and Sb, X is at least one selected from the group consisting of OH, F, Cl, Br, I and At, 0≦y<1, 0<n<3, and 0<m<3.

* * * * *